US007910680B2

(12) United States Patent
White et al.

(10) Patent No.: US 7,910,680 B2
(45) Date of Patent: Mar. 22, 2011

(54) REACTIVE (METH)ACRYLATE MONOMER COMPOSITIONS AND PREPARATION AND USE THEREOF

(75) Inventors: Jerry E. White, Lake Jackson, TX (US); Jim D. Earls, Lake Jackson, TX (US); Peter S. Martin, Houston, TX (US); Mike B. McIntosh, Midland, MI (US); Richard M. Wehmeyer, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 946 days.

(21) Appl. No.: 11/789,755

(22) Filed: Apr. 25, 2007

(65) Prior Publication Data

US 2008/0108728 A1   May 8, 2008

Related U.S. Application Data

(63) Continuation-in-part of application No. PCT/US2006/043689, filed on Nov. 8, 2006.

(51) Int. Cl.
*C08F 251/00* (2006.01)
*C08F 251/02* (2006.01)
*C08F 2/46* (2006.01)

(52) U.S. Cl. ........ 527/312; 527/313; 527/314; 527/300; 527/303; 527/311; 527/100; 527/102; 527/600; 527/602; 527/603; 527/604; 526/72; 526/75; 526/310; 526/312; 522/173; 522/178; 522/181

(58) Field of Classification Search .................. 527/100, 527/102, 600, 602, 603, 604, 300, 311, 303, 527/312, 313, 314; 526/72, 310, 312, 75; 522/173, 178, 182, 87, 88, 89
See application file for complete search history.

(56) References Cited

U.S. PATENT DOCUMENTS

| | | | |
|---|---|---|---|
| 2,129,722 A | 9/1938 | Woodhouse | |
| 2,712,558 A | 7/1955 | Vander Wal et al. | |
| 3,290,387 A | 12/1966 | Bernardy et al. | |
| 3,366,613 A | 1/1968 | Kelley | |
| 3,450,741 A | 6/1969 | Becke et al. | |
| 3,713,864 A | 1/1973 | Ackerman et al. | |
| 3,917,661 A | 11/1975 | Pruett et al. | |
| 4,052,461 A | 10/1977 | Tinker et al. | |
| 4,122,290 A | 10/1978 | Immel et al. | |
| 4,128,600 A | 12/1978 | Skinner et al. | |
| 4,216,343 A | 8/1980 | Rogier | |
| 4,216,344 A | 8/1980 | Rogier | |
| 4,229,562 A | 10/1980 | Rogier | |
| 4,243,818 A | 1/1981 | Rogier | |
| 4,304,945 A | 12/1981 | Rogier | |
| 4,356,128 A | 10/1982 | Rogier | |
| 4,423,162 A | 12/1983 | Peerman et al. | |
| 4,496,487 A | 1/1985 | Peerman et al. | |
| 4,519,065 A | 5/1985 | Lewis et al. | |
| 4,626,582 A | 12/1986 | Virnig et al. | |
| 4,723,047 A | 2/1988 | Bahrmann et al. | |
| 5,312,889 A | 5/1994 | Frische et al. | |
| 5,360,836 A | 11/1994 | Chevallier et al. | |
| 6,174,948 B1 | 1/2001 | Thames et al. | |
| 6,203,720 B1 | 3/2001 | Thames et al. | |
| 6,235,916 B1 | 5/2001 | Thames et al. | |
| 6,245,829 B1 | 6/2001 | Meij et al. | |
| 6,624,223 B1 | 9/2003 | Thames et al. | |
| 2005/0070620 A1 | 3/2005 | Herrington et al. | |

FOREIGN PATENT DOCUMENTS

| | | | |
|---|---|---|---|
| CA | 2162083 | | 11/1995 |
| DE | 2002-10225367 | | 6/2002 |
| IN | 154467 | | 7/1980 |
| JP | 50069143 | | 10/1973 |
| JP | 2004075880 A | * | 3/2004 |
| JP | 2004168740 A | * | 6/2004 |
| JP | 2004185653 A | * | 7/2004 |
| WO | WO 03/093215 A1 | | 11/2003 |
| WO | WO 2004/096744 A2 | | 11/2004 |

OTHER PUBLICATIONS

B.S. Sitaramam, P.C. Chatterjee, M.A. Sivasamban, *Use of Castor-based Products in Formulating UV-curable Coatings*, Paintindia (1986), 36(1), 17-18.
R. Subramanian, S.H. Rachakonda, W.W. Smith, S.F. Thames, *Ultraviolet Curable Coatings Using CAM*, Polymer Preprints (ACS, Division of Polymer Chemistry) (1999), 40(2), 762-763.
M.A. Ali, T.L. Ool, A. Salmiah, U.S. Isiaku, Mond, Z.A. Ishak, *New Polyester Acrylate Resins From Palm Oil For Wood Coating Applications*, Journal of Applied Polymer Science, vol. 79, 2156-2163, 2001.
P.B. O'Connor, D.P. Little and F.W. McLafferty, *Isotopic Assignment in Large-Molecule Mass Spectra by Fragmentation of a Selected Isotopic Peak*, Analytical Chemistry, vol. 68, No. 3, J. Am. Chem. Soc., (1996) 542-545.
S.F. Thames, Haibin Yu, T.P. Schuman, Min D. Wang, *Acrylated lesquerella oil in ultraviolet cured coatings*, Progress in Organic Coatings, vol. 28, (1996) 299-305.
S.F. Thames, "Solventless Emulsion Polymers in Coatings." *Proceedings of the Twenty-Fifth International Waterborne, High-Solids, and Powder Coatings Symposium*, New Orleans, LA, 1998, 305-320.
A.I. McKenna, *Fatty Amides—Synthesis, Properties, Reactions and Applications*, Humko Chemical Division of Witco Chemical Corporation (1982), pp. v-67 and pp. 69-195.

* cited by examiner

*Primary Examiner* — Sanza L McClendon

(57) ABSTRACT

The present invention relates to new (meth)acrylate compositions, their preparation and their use in ultraviolet light curable applications such as coatings, inks and adhesives.

9 Claims, No Drawings

REACTIVE (METH)ACRYLATE MONOMER COMPOSITIONS AND PREPARATION AND USE THEREOF

This application is a C.I.P. of PCT/US06/43689 filed Nov. 8, 2006.

The present invention relates generally to novel reactive (meth)acrylate monomer compositions and processes used to prepare such compositions. The present invention relates more particularly to such reactive monomer compositions that are derived from renewable raw material sources such as unsaturated seed or vegetable oils. The present invention relates still more particularly to such reactive monomer compositions that contain at least one of an amide moiety, an ester moiety or a triglyceride moiety. The present invention also relates to the use of such reactive monomer compositions in preparing coatings, particularly curable coatings and especially ultraviolet light (UV) curable coatings. The reactive monomer compositions may also be used in preparing adhesive compositions or sealant compositions.

Conventional acrylate resins or compositions such as epoxy acrylate resins evidence a number of shortcomings when used in UV curable coating applications. Resultant UV-cured coatings tend to be brittle rather than flexible and lack adequate adhesion to coated substrates for most, if not all, desired applications. Skilled artisans understand that impact testing, such as that detailed below, provides an indication of coating adhesion and flexibility. More particularly, lack of coating delamination after impact testing indicates at least minimal acceptable adhesion. If an examination of a coating or film after impact testing reveals few, preferably no, visible cracks, skilled artisans view the coating or film as having at least minimum acceptable flexibility. In addition, conventional acrylate resins, especially epoxy acrylate resins, have an undiluted viscosity in excess of 4,000 centipoise (cps) (4.0 pascal seconds (Pa·s)). In order to use such resins in, for example, UV-curable coatings, one must add a diluent such as tri(propylene glycol)diacrylate to reduce coating composition viscosity to a practical room temperature (nominally 25° C.) coating viscosity of no more than 4,000 cps (4.0 Pa·s) and preferably no more than 2500 cps (2.5 Pa·s).

Those who use reactive monomers or reactive monomer compositions, especially those who use such monomers or monomer compositions in UV curable compositions, desire reactive monomers that can be used with little or, preferably, no diluent even when the UV curable composition includes, for example, up to forty percent by weight (40 wt %), based upon total coating weight, of a solid, particulate additive such as a pigment. They also desire that such compositions yield a UV-cured coating with an improvement in at least one of impact resistance, hardness and scratch resistance relative to UV-cured coatings prepared using conventional acrylate resins such as an epoxy acrylate. Other desirable, but optional, features include coating compositions that, when cured, yield flexible coatings or films, preferably with improvements in at least one of moisture resistance and stain resistance relative to films made from currently available reactive monomers.

U.S. Pat. No. 3,713,864 discloses printing ink compositions comprising an epoxidized soybean oil acrylate, or a derivative thereof, conventional colorants (e.g. a pigment such as Lithol Rubine (red), Benzidine Yellow, Green Shade Phthalocyanine Blue, Iron Blue and Carbon Black (channel or furnace) and a radiation sensitizer (e.g. acetophenone or benzophenone). U.S. Pat. No. 3,713,864 also discloses a method of printing with such ink compositions that comprises exposing the ink compositions to an amount of actinic radiation sufficient to polymerize polymeric constituents of the ink compositions to a non-offsetting state and resulting printed substrates prepared by such method.

U.S. Pat. No. 3,713,864 teaches preparation of epoxidized soybean oil or epoxidized linseed oil acrylates at column 2, line 54 through column 3, line 7. Preparation begins by epoxidizing soybean oil or linseed oil using a conventional epoxidizing agent such as peracetic acid or hydrogen peroxide. Acrylation of the epoxidized oil occurs via, for example, reaction of the epoxidized oil with acrylic acid at a temperature of 100 degrees centigrade (° C.) in the presence of a polymerization inhibitor such as phenothiazine. U.S. Pat. No. 3,713,864 also teaches reaction of a bisphenol A-epichlorohydrin epoxy resin with acrylic acid or methacrylic acid.

U.S. Pat. No. 4,243,818 defines "hydroformylation" at column 5, lines 8-12 as the production of aldehydes from unsaturated compounds by reaction with hydrogen and carbon monoxide in the presence of a catalyst. The preferred unsaturated compound, per column 5, lines 36-38, is oleyl alcohol, but linoleyl alcohol or linolenyl alcohol may also be used as the unsaturated compound. At column 9, lines 52-58, '818 teaches use of an acid halide such as acryloyl chloride to convert the alcohols to their corresponding unsaturated esters (e.g. an acrylate or a methacrylate).

U.S. Pat. No. 4,128,600 discloses interpenetrating dual cure resin compositions. Curable resin compositions contain a radiation-sensitive reactive diluent, a saturated polyol and an isocyanate. Exposure of the composition to radiation effects curing of the reactive diluent. Subsequent thermal curing forms urethane linkages. In accord with column 3, lines 38-44, the reactive diluent may be a fully substituted polyacrylate or polymethacrylate of a polyfunctional alcohol. At column 5, lines 10-13, '600 explicitly states that the reactive diluent must not contain hydroxyl, amine, carboxyl, primary and secondary amides or isocyanate functional groups. Polyfunctional alcohols include, per column 5, lines 43-46, normal and isomeric forms of nonyl, decyl, undecyl, dodecyl, tridecyl and tetradecyl alcohols. At column 18, lines 43-45, '600 defines pencil hardness testing as an indication of "the scratch resistance of the resin coating with 9H being the hardest and 6B being the softest".

U.S. Pat. No. 4,626,582 discusses acryloxymethyl substituted fatty compounds represented by a formula $CH_3$—$CH_2)_m$—$((Y)$—$C$—$(Z))$—$(CH_2)_n$—$X$ wherein m and n are integers, n is greater than 3 and the sum of m and n ranges from 7 to 19; Y is a hydrogen, methylol or acryloxymethyl group; and one of X and Z is acryloxymethyl and the other is selected from (a) —CN, (b) —C(O)—$NR^1R^2$, (c) —C(O)—$OR^3$, or (d) —$CH_2$—$NR^4R^5$, wherein $R^1$, $R^2$, $R^3$ are independently lower alkyl (1 to 4 aliphatic carbon atoms) provided that $R^1$ and $R^2$ may together constitute a divalent hydrocarbon having 4, 5 or 6 aliphatic carbons or 3, 4 or 5 aliphatic carbon atoms and one hetero atom or group; $R^4$ is lower acyl; and $R^5$ is hydrogen or lower alkyl; provided that when X is acryloxymethyl, Y is hydrogen. Per column 2, lines 9-14, such compounds may be used in preparation of curable coatings. Column 4, lines 16-31 presents teachings related to radiation curing of such coatings.

U.S. Pat. No. 5,312,889 discloses at column 1, lines 23-28, that "hydroxyfatty acids in natural fats and oils and their derivatives, or hydroxyfatty acids or aminofatty acids that can be produced from reactive fatty acids (e.g., oleic acid, linoleic acid) are particularly suitable for making technically useful products, especially polymers and plastics". According to column 2, lines 52-57, "amino-group-containing fatty acid residues . . . are obtained from unsaturated fatty acid esters, using known chemical methods, for example through addition to the double bond of a hydrogen halide such as hydrobromic acid and subsequent nucleophilic substitution of ammonia for the halide".

As stated in column 1, lines 12-21, U.S. Pat. No. 6,174,948 relates to novel latex or emulsion compositions containing either a vinyl ether, vinyl ester, or an acrylic ester of a long-chain olefinic monomer derived from semi- and/or non-drying oils, a process for making the same, and utility of such compositions in coatings, adhesives, and inks which have essentially no volatile organic components (VOCs) and feature enhanced application and performance properties. Per column 5, lines 5-9, illustrative examples of semi-drying oils include safflower oil, sunflower oil, soybean oil, and tobacoseed oil, and illustrative examples of non-drying oils include cottonseed oil, coconut oil, rapeseed oil, castor oil, and lesquerella oil. At column 16, lines 36-43, '948 teaches that preferred starting materials include substituted or unsubstituted vinyl esters of fatty acids, vinyl ethers of fatty alcohols, and acrylates and acrylamides of fatty alcohols or fatty amines. Representative examples of such starting materials, without limitation, include vinyl ester of oleic acid, oleyl acrylate, oleyl methacrylate, oleyl acrylamide, oleyl methacrylamide, and vinyl oleyl ether. '948 Example 1 reacts methacryloyl chloride and oleyl alcohol in the presence of triethyl amine to yield oleyl methacrylate. '948 Example 2 replicates Example 1, but substitutes acryloyl chloride for methacryloyl chloride. '948 Example 8 uses the oleyl acrylate of Example 2 in a UV-curable formulation.

U.S. Pat. No. 6,245,829 discusses radiation-curable compositions comprising a mono- or multi-valent carboxylic ester of a β-hydroxyalkylamide group containing compound, in which the carboxylic ester is derived from an alpha, beta(α, β)-ethylenically unsaturated carboxylic acid. Such a composition may be prepared by reacting a β-hydroxyalkylamide with an unsaturated carboxylic acid chloride, anhydride or ester in accord with column 2, lines 47-50. Column 3, lines 42-48, notes that, after curing, the coatings prepared from such compositions have many desired properties such as, for example, good chemical properties (resistance to solvents, acids, alkalis and moisture), good optical properties and appearance, good mechanical properties (such as hardness, flexibility, adhesion, abrasion resistance, strength and durability), good thermal stability and good weatherability.

As used throughout this specification, definitions presented in this paragraph, in succeeding paragraphs or elsewhere in the specification, have meanings ascribed to them where first defined. Accordingly, "hydrocarbyl" means a monovalent straight or branched chain, saturated or unsaturated predominantly hydrocarbon moiety having from one to 60 carbon atoms ($C_1$-$C_{60}$). Hydrocarbylene means a polyvalent straight or branched chain, saturated or unsaturated predominantly hydrocarbon moiety having one to 60 carbon atoms ($C_1$-$C_{60}$).

"(Meth)acrylate" is a collective term for α, β-unsaturated acylates that includes esters of acrylic acid (alkyl acrylate resins) where acryloyl chloride is used as an acylating agent and esters of methacrylic acid (alkyl methacrylate resins) where methacryloyl chloride is used as an acylating agent.

"Fatty acid" means a predominantly aliphatic acid with more than 8 carbons.

"Fatty acid ester" means a predominantly aliphatic ester with more than 8 carbons.

When ranges are stated herein, as in a range of from 2 to 10, both end points of the range (e.g. 2 and 10) are included within the range unless otherwise specifically excluded.

A first aspect of the present invention is a reactive monomer composition comprising an amide poly-α, β-unsaturated acylate represented by formula I:

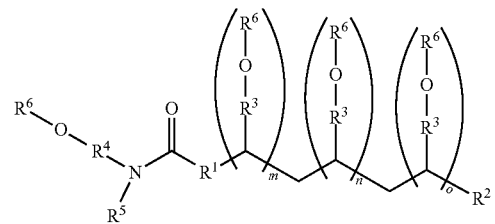

Formula I

Wherein $R^1$ is a hydrocarbylene moiety; $R^2$ is hydrogen or a hydrocarbyl moiety; $R^3$ is nil or a hydrocarbylene moiety; $R^4$ is a hydrocarbylene moiety; $R^5$ is H, a hydrocarbyl moiety or a moiety represented by Formula II:

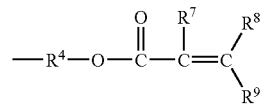

Formula II wherein $R^4$ is as defined above and $R^7$, $R^8$ and $R^9$ are independently hydrogen or a hydrocarbyl moiety; $R^6$ is a moiety having Formula III:

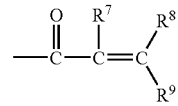

Formula III wherein $R^7$, $R^8$ and $R^9$ are independently defined as above; and m, n, and o are independently 0 or 1, provided, however that a sum of m, n and o is a positive integer greater than zero (e.g. 1, 2 or 3).

A second aspect of the present invention is a process to prepare the reactive monomer of the first aspect. The process comprises sequential steps:

a. reacting an alkanolamine with a compound having at least one reactive hydroxy group or moiety, the compound being selected from the group consisting of triglycerides, fatty acids and fatty acid esters, to convert the compound to an amide polyol; and b. reacting the amide polyol with an α, β-unsaturated acylating agent to convert the amide polyol to an amide poly-α, β-unsaturated acylate.

A third aspect of the present invention is a reactive monomer composition comprising a poly-α, β-unsaturated acylate represented by either of:

Formula IV

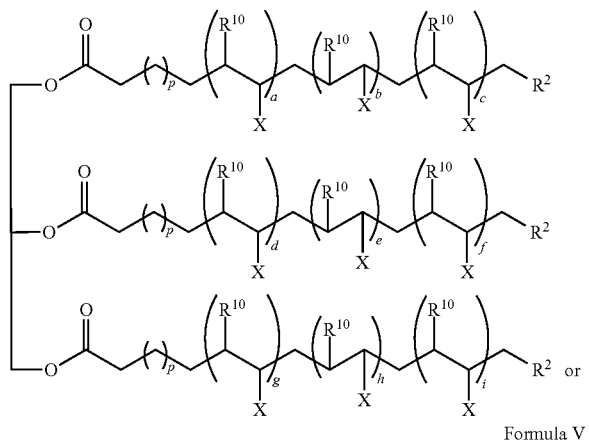

Formula V

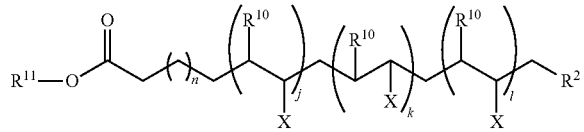

wherein $R^2$ is as previously defined; $R^{10}$ is a moiety of the following formula:

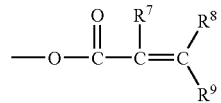

wherein $R^7$, $R^8$ and $R^9$ are as previously defined; $R^{11}$ is hydrogen or a hydrocarbyl moiety; n and p are 0 or a positive integer within a range of from 1-20; a, b, c, d, e, f, g, h, i, j, k and l are independently 0 or 1, provided however that at least one of a sum of a, b, c, d, e, f, g, h and i or a sum of j, k and l is a positive integer greater than zero (e.g. 1); and X is:

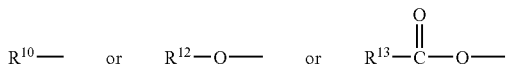

wherein $R^{10}$ is defined as above, $R^{12}$ and $R^{13}$ are independently hydrogen or a hydrocarbyl moiety.

A fourth aspect of the present invention is a process for preparing the reactive poly-α, β-unsaturated acylate of the third aspect. The process comprises sequential steps:
(a) reacting an epoxy-functionalized vegetable oil, epoxidized fatty acid or epoxidized fatty acid ester with water, a carboxylic acid or an alcohol in the presence of an acid catalyst to form a polyol; and
(b) reacting the polyol of step (a) with an α, β-unsaturated acylating agent to form a reactive monomer composition comprising a poly-α, β-unsaturated acylate.

A fifth aspect of the present invention is a process for preparing a reactive α, β-unsaturated acylate monomer composition, the process comprising sequential steps:
(a) polymerizing at least one fatty acid or fatty acid ester, the fatty acid or fatty acid ester containing at least one reactive hydroxy moiety, with a polyol initiator to form a hydroxy-functionalized aliphatic polyester;
(b) reacting the polyester of step (a) with an α, β-unsaturated acylating agent to form a reactive α, β-unsaturated acylate.

A sixth aspect of the present invention is a reactive α, β-unsaturated acylate prepared in accord with the process of the fifth aspect.

A seventh aspect of the invention is a UV-curable composition comprising the reactive monomer composition of the first aspect or the reactive acylate of the third or sixth aspect of the invention.

An eighth aspect of the present invention is a UV-curable ink, adhesive composition or coating composition comprising the UV-curable composition of the seventh aspect.

A ninth aspect of the present invention is an UV-cured ink, adhesive composition or coating composition prepared from the corresponding composition of the eighth aspect.

The reactive monomer composition of the first aspect comprises or includes an amide poly-α, β-unsaturated acylate represented by formula I:

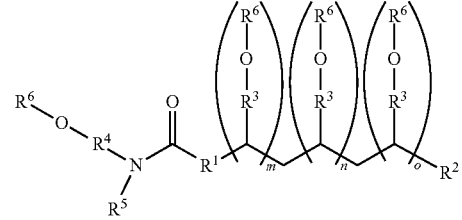

Wherein $R^1$ is a hydrocarbylene moiety; $R^2$ is hydrogen or a hydrocarbyl moiety; $R^3$ is nil or a hydrocarbylene moiety; $R^4$ is a hydrocarbylene moiety; $R^5$ is H, hydrocarbyl moiety or a moiety represented by Formula II:

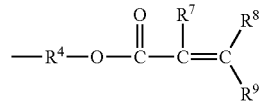

wherein $R^4$ is as defined above and $R^7$, $R^8$ and $R^9$ are independently hydrogen or a hydrocarbyl moiety; $R^6$ is a moiety having Formula III:

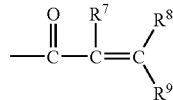

wherein $R^7$, $R^8$ and $R^9$ are independently defined as above; and m, n, and o are independently 0 or 1, provided that a sum of m, n and o is a positive integer greater than 0 (e.g. 1, 2 or 3).

In a preferred variation of the amide, $R^1$ is a hydrocarbylene moiety; $R^2$ is hydrogen or hydrocarbyl; $R^3$ is nil or methylene; $R^4$ is ethylene or propylene; $R^5$ is hydrogen, methyl or a moiety represented by Formula II wherein $R^4$ is ethylene, $R^7$ is hydrogen or methyl and $R^8$ and $R^9$ are hydrogen; and $R^6$ is a moiety represented by Formula III wherein $R^7$ is hydrogen or methyl and $R^8$ and $R^9$ are hydrogen.

Specific examples of suitable (meth)acrylate-substituted amides include methyl 11-hydroxyundecanoate amide acrylate, 12-hydroxystearate amide acrylate, methyl 12-hydroxystearate amide acrylate and ricinolamide acrylate.

Preparation of the amide poly-α, β-unsaturated acylate comprises at least two sequential steps a. and b. Step a. comprises reacting an alkanolamine with a compound having at least one reactive hydroxy moiety, the compound being selected from the group consisting of triglycerides, fatty acids or fatty acid esters, to convert the compound to an amide polyol. Step b. comprises reacting the amide polyol with an α, β-unsaturated acylating agent to convert the amide polyol to an amide poly-α, β-unsaturated acylate.

In step a., the alkanolamine and the compound are present in a molar ratio of alkanol amine to compound that falls within a range of from 4:1 to 1:1. The range is preferably from 3:1 to 1:1, more preferably from 2:1 to 1:1, and still more preferably from 2:1 to 1.5:1.

Step a. is an endothermic reaction that requires one to heat reactants to a temperature of at least 60° C., preferably at least 80° C., still more preferably at least 100° C. The temperature is preferably no more than 150° C., more preferably no more than 130° C. and still more preferably no more than 120° C.

Step a. preferably includes use of a non-reactive solvent for the reactants. The solvent is used in an amount sufficient to place solid reactants in solution at the temperature specified above. The solvent is preferably selected from toluene, chloroform and ethyl ether, with toluene being most preferred.

Step a. preferably includes use of a catalyst such as potassium hydroxide. More preferably a solution 30 wt % of potassium hydroxide in methanol. While use of methanol is optional, it is also preferred as it aids in dissolution of the catalyst. Other catalysts which can be used include sodium hydroxide and sodium methoxide. The catalyst is preferably used in an amount within a range of from 0 parts by weight (pbw) to 5 pbw per 100 pbw diethanolamine.

Recovery of the amide polyol produced in step a. occurs by standard procedures such as those detailed in the examples provided below. Such procedures include, washing with an aqueous salt solution such as a solution 2 wt % sodium chloride in water, the weight percentage being based upon total solution weight, drying with anhydrous magnesium sulfate and rotary evaporation to remove toluene.

In step b., the amide polyol and the α, β-unsaturated acylating agent are present in a molar ratio of amide polyol to α, β-unsaturated acylating agent that falls within a range of from 1:1 to 0.2:1. The range is preferably from 0.75:1 to 0.2:1, more preferably from 0.5:1 to 0.2:1, and still more preferably from 0.4:1 to 0.2:1.

Like step a., step b. preferably includes use of a non-reactive solvent for the reactants. The solvents specified for step a. also work for step b.

Step b. is an exothermic reaction that requires one to cool reactants to a temperature of no more than 30 degrees centigrade (° C.), preferably no more than 20° C., still more preferably no more than 10° C. The temperature is preferably at least 0° C., and more preferably at least 5° C. At temperatures below 0° C. (e.g. −5° C.), reactants tend to solidify, thereby interfering with further processing.

Recovery of the amide poly-α, β-unsaturated acylate produced in step b. occurs by standard procedures such as those detailed in the examples provided below, especially Example 2.

When using a compound other than castor oil or a castor oil derivative, preparation of the amide poly-α, β-unsaturated acylate preferably includes a precursor step that precedes step a. and comprises at least partial reductive hydroformylation of a starting material selected from the group consisting of unsaturated vegetable oils, fatty acids and fatty acid esters.

U.S. Pat. No. 4,243,818, the teachings of which are incorporated herein by reference, teaches hydroformylation. When used, a precursor step that precedes step a. includes hydroformylation sufficient to functionalize or react with greater than zero percent of unsaturation in the starting material up to 100 percent of such unsaturation. The hydroformylation is preferably sufficient to react with at least (≧) 20 percent (%) of unsaturation, more preferably ≧50% of unsaturation and most preferably ≧80% of unsaturation.

Additional references, the teachings of which are incorporated herein to the maximum extent permitted by law, that discuss hydroformylation include U.S. Pat. No. 4,423,162 (especially Ex 34), U.S. Pat. No. 4,723,047, Canadian Patent Application (CA) 2,162,083, WO 2004/096744, U.S. Pat. No. 4,496,487, U.S. Pat. No. 4,216,344, U.S. Pat. No. 4,304,945 and U.S. Pat. No. 4,229,562.

The teachings of U.S. Pat. No. 4,423,162, especially those found at column 3, line 50 through column 4, line 36, are particularly instructive for those seeking to practice reductive hydroformylation. In that portion, one prepares a hydroxy ester monomer starting material prepared by hydrogenating a hydroformylated unsaturated carboxylic acid or ester. One may obtain suitable unsaturated acids by splitting a triglyceride into its respective component fatty acids. U.S. Pat. No. 4,423,162 notes that sources of fatty acids include fatty oils such as tallow and most plant sources particularly soybean, sesame, sunflower, tall oil and other similar materials, but prefers starting fatty acids that are in the form of a methyl ester.

U.S. Pat. No. 4,423,162 teaches that introduction of a hydroxymethyl group can be readily accomplished by a hydroformylation process utilizing either cobalt or rhodium catalysts, followed by hydrogenation of the formyl group to obtain the hydroxymethyl group by catalytic methods or by chemical reduction. In doing so, U.S. Pat. No. 4,423,162 also refers to, and incorporates by reference, procedures described in detail in U.S. Pat. No. 4,216,343, U.S. Pat. No. 4,216,344, U.S. Pat. No. 4,304,945, and U.S. Pat. No. 4,229,562.

Preferred α, β-unsaturated acylating agents include acid halides. Especially preferred α, β-unsaturated acylating agents include acryloyl chloride when one is preparing acrylate-containing compositions or methacryloyl chloride when one is preparing methacrylate-containing compositions. If one desires a mixture or blend of acrylate moieties and methacrylate moieties, one can use a mixture of acryloyl chloride and methacryloyl chloride.

When the compound that reacts with an alkanolamine in step a. is derived from an unsaturated vegetable oil, the compound is preferably a hydroxy-functionalized vegetable oil, the unsaturated vegetable oil being selected from the group consisting of safflower oil, sunflower oil, soybean oil, linseed oil, peanut oil, olive oil, tobaccoseed oil, cottonseed oil, coconut oil, rapeseed oil, canola oil, corn oil, lesquerella oil or a modified version of any such oil. Modifications of such oils include reductive hydroformylation.

When the compound that reacts with an alkanolamine in step a. is derived from a fatty acid, the compound is preferably a hydroxy-functionalized acid, the acid being selected from oleic acid, linoleic acid, and linolenic acid.

When the compound that reacts with an alkanolamine in step a. is derived from a fatty acid ester, the compound is preferably a hydroxy-functionalized ester, more preferably a hydroxy-functionalized fatty acid methyl ester, especially a hydroxy-functionalized fatty acid methyl ester wherein the methyl ester is selected from the group consisting of methyl oleate, methyl 10-undecenoate, methyl 9-decenoate, methyl linolenate, and methyl linoleate.

Preferred starting materials include hydroxymethyl fatty acids, hydroxymethyl fatty acid esters, castor oil and castor oil derivatives. Especially preferred starting materials include those selected from the group consisting of hydroxymethyl stearate, hydroxymethyl methyl stearate, ricinoleic acid and ricinoleic acid esters.

Preferred alkanolamines include at least one of ethanolamine, 1,2-propanolamine or diethanolamine.

The reactive monomer composition of the third aspect comprises a poly-α, β-unsaturated acylate represented by either of:

Formula IV

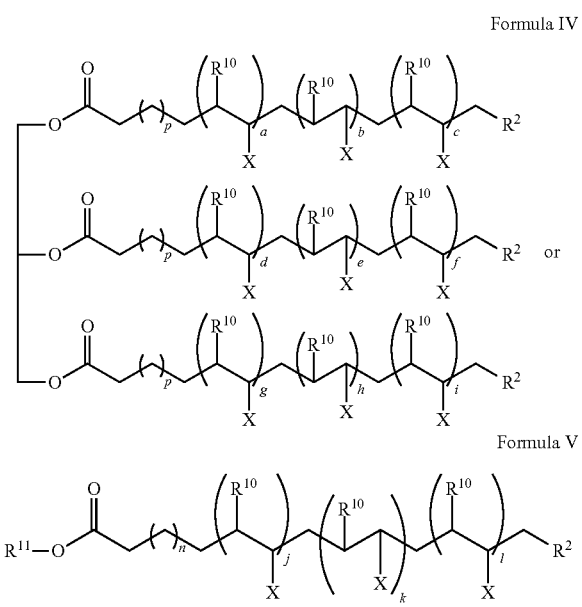

Formula V wherein $R^2$ is as previously defined; $R^{10}$ is a moiety of the following formula:

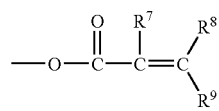

wherein $R^7$, $R^8$ and $R^9$ are as previously defined; $R^{11}$ is hydrogen or a hydrocarbyl moiety; n and p are 0 or a positive integer within a range of from 1-20; a, b, c, d, e, f, g, h, i, j, k and l are independently 0 or 1, provided however that at least one of a sum of a, b, c, d, e, f, g, h and i or a sum of j, k and l is a positive integer (e.g. 1, 2, 3, 4 or 5) greater than zero; and X is:

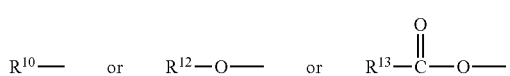

wherein $R^{10}$ is defined as above, $R^{12}$ and $R^{13}$ are independently hydrogen or a hydrocarbyl moiety.

The poly-α, β-unsaturated acylate of the third aspect is preferably prepared a process that comprises sequential steps (a) and (b). Step (a) comprises reacting at least one first reactant selected from an epoxy-functionalized vegetable oil, an epoxidized fatty acid or an epoxidized fatty acid ester with at least one second reactant selected from water, a carboxylic acid or an alcohol in the presence of an acid catalyst to form a polyol. Sequential step (b) comprises reacting the polyol of step (a) with an α, β-unsaturated acylating agent to form a reactive monomer composition comprising a poly-α, β-unsaturated acylate. The α, β-unsaturated acylating agent is preferably selected from those disclosed above.

Preferred epoxy-functionalized vegetable oils suitable for use as a first reactant include vernonia oil, epoxidized soybean oil, or epoxidized linseed oil.

Preferred epoxidized fatty acids suitable for use as a first reactant include epoxidized undecenoic acid, and epoxidized oleic acid.

Preferred epoxidized fatty acid esters suitable for use as a first reactant include epoxidized methyl oleate, epoxidized methyl 10-undecenoate and epoxidized methyl 9-decenoate.

Preferred carboxylic acids suitable for use as a second reactant include acetic acid and formic acid.

Preferred alcohols suitable for use as a second reactant include methanol, ethanol, propanol and butanol.

Preferred acid catalysts include ion exchange references, preferably a cation exchange resin such as DOWEX™ cation exchange resin MSC-1 (The Dow Chemical Company) and mineral acids (e.g. sulfuric acid).

Step (a) effectively opens epoxy ring structures present in the first reactant (e.g. an epoxy-functionalized or epoxidized vegetable oil) and produces a polyol. Step (a) includes heating, with stirring, and preferably under an inert gaseous atmosphere (e.g. nitrogen), a combination of the first reactant, the second reactant and an acid catalyst.

Step (a) is an endothermic reaction that requires one to heat reactants to a set point temperature of at least 25° C., preferably at least 50° C., still more preferably at least 65° C. The temperature is preferably no more than 150° C., more preferably no more than 120° C. and still more preferably no more than 100° C.

As an alternative to nitrogen, one may use another inert gas such as helium, or a mixture of inert gases.

Recovery of the ring-opened first reactant produced in step (a) occurs by standard procedures such as those detailed in the examples provided below, especially Example 6. Vacuum filtration with a nitrogen sweep followed by vacuum distillation provides quite satisfactory results.

Sequential step (b) comprises reacting the polyol of step (a) with an α, β-unsaturated acylating agent to form a reactive monomer composition comprising a poly-α, β-unsaturated acylate. Step (b) largely replicates step b. detailed above save for substituting the polyol produced in step (a) for the amide polyol produced in step a. Example 7 below illustrates step (b) and details recovery of the poly-α, β-unsaturated acylate.

The process of the fifth aspect of the present invention yields the reactive α, β-unsaturated acylate monomer composition of the sixth aspect. The process comprises sequential steps [a] and [b]. Step [a] comprises polymerizing at least one first reactant that contains at least one reactive hydroxy moiety, the first reactant being a fatty acid or a fatty acid ester, with a polyol initiator to form a hydroxy-functionalized aliphatic polyester. Sequential step [b] comprises reacting the hydroxy-functionalized aliphatic polyester of step [a] with an α, β-unsaturated acylating agent to form a reactive α, β-unsaturated acylate. The α, β-unsaturated acylating agent is preferably selected from those disclosed above.

Polymerization of a first reactant with a polyol initiator preferably occurs at a temperature within a range of from 168° C. to 230° C., more preferably within a range of from 190° C. to 200° C. The polymerization preferably occurs under an inert gaseous blanket (also referred to as in the presence of an inert gaseous medium) in order to minimize color formation.

The reaction that takes place in step [b] preferably occurs in an inert gaseous (e.g. nitrogen) atmosphere at a temperature within a range of from 0° C. to 30° C., more preferably within a range of from 5° C. to 20° C., and most preferably from 5° C. to 10° C. When rotary evaporation is used to remove a solvent (e.g. toluene) as part of product recovery, limiting temperature during rotary evaporation to a maximum of 60° C. yields satisfactory results.

The first reactant may be prepared by at least partial hydroformylation, which is defined above, provided that a minimum level of partial hydroformylation for the fifth aspect is 80% of unsaturation present in the first reactant prior to hydroformylation.

Preferred fatty acids suitable for use as a first reactant in the process of the fifth aspect include 12-(hydroxymethyl)stearic acid, (hydroxymethyl)stearic acid diol, and (hydroxy methyl) stearic acid triol.

Preferred fatty acid esters suitable for use as a first reactant in the process of the fifth aspect include 12-(hydroxymethyl) stearate, (hydroxymethyl)stearate diol, and (hydroxy methyl) stearate triol.

Preferred polyol initiators include glycerol, glycerol ethoxylate, polyethylene glycol, and polypropylene glycol.

The amide poly-$\alpha$, $\beta$-unsaturated acylate and the $\alpha$, $\beta$-unsaturated acylate monomer compositions disclosed above have practical utility as UV-curable components of UV-curable compositions such as UV-curable ink compositions, UV-curable adhesive compositions and UV-curable coating compositions. Such compositions, subsequent to exposure to UV-curing conditions sufficient to effect curing of the compositions, yield commercially desirable results in terms of, respectively, cured inks, cured adhesives and cured coatings.

Compositions of the present invention may include one or more photoinitiators. The general classes of photoinitiators which are preferred include benzophenones, $\alpha$-hydroxy ketones, $\alpha$-amino ketones, and phosphine oxides.

Compositions of the present invention may include one or more non-reactive components conventionally added to UV-curable coating compositions. Such non-reactive components include, without limitation, pigments, fillers, stabilizers and solvents.

In preparing an ink based upon reactive monomers of the present invention, one may use any conventional coloring agent or pigment known in the art. For example, various organic pigments and inorganic pigments may be broadly used as coloring agents, but non-toxic anticorrosive pigments are preferred. Examples of such pigments include phosphate-type anticorrosive pigments such as zinc phosphate, calcium phosphate, aluminum phosphate, titanium phosphate, silicon phosphate, and ortho- and fused phosphates of these; molybdate-type anticorrosive pigments such as zinc molybdate, calcium molybdate, calcium zinc molybdate, potassium zinc molybdate, potassium zinc phosphomolybdate and potassium calcium phosphomolybdate; and borate-type anticorrosive pigments such as calcium borate, zinc borate, barium borate, barium meta-borate and calcium meta-borate. Selection of an appropriate amount of coloring agent or pigment depends upon whether a given end-use application for reactive monomers of the present invention requires or lends itself to coloration imparted by pigments or coloring agents. For radiation-curable printing inks, pigment loadings as high as 40 percent by weight, based upon total weight of such inks, yield satisfactory results. For end use applications requiring a colorless product, pigment or coloring agent may be omitted.

Analytical Procedures

The analytical procedures used for $H^1NMR$, $^{13}CNMR$, FTIR are based on standard methods such as described in an ACS Professional Reference Book entitled "Spectroscopy of Polymers" by Jack L. Koening. Other test methods used herein are described below.

Determine % hydroxy via titration in accord with ASTM Test Method D4274.

Coating Thickness

Use a Fisher Multiscope thickness tester to determine thickness of non-magnetic coatings deposited on ferromagnetic substrates. The Fisher Multiscope includes a probe and operates via magnetic induction to indicate coating thickness after placing the probe against the coating and activating the Multiscope. Coating thickness values reported herein represent an average of 15 coating thickness measurements.

Methyl Ethyl Ketone (MEK) Double Rubs—ASTM Method D 5402

Pass the rounded end or peen of a two pound (4.4 kilograms (kg)) ball-peen hammer covered with 8 ply gauze soaked in MEK back and forth over the surface of a coated panel until the coating fails. Use only weight of the hammer and that force needed to guide the gauze-covered peen across the coating in this test. Coating failure occurs upon exposure of a panel substrate beneath the coating. Use acidic copper sulfate to verify substrate exposure and coating failure. Replicate the test two times, determine the arithmetic mean of such testing and report that mean as "Coating MEK Double Rub Failure Number".

Film Hardness by Pencil Test—ASTM Method D 3363

Place a coated panel on a firm horizontal surface. Have an operator hold a pencil of known hardness firmly against the coating or film at a 45° angle and push the pencil away from the operator's body in a ¼ inch (6.35 mm) stroke. Begin this test with the softest lead pencil (6B) and continue testing with pencils of progressively harder lead (toward 9H) until the stroke causes the pencil to cut into or gouge the film or coating. Report coating pencil hardness by hardness of the lead of that pencil immediately preceding the pencil that cuts into or gouges the coating.

Fingernail Scratch Test

In this subjective test, an operator draws his or her fingernail across a coating surface using modest pressure and then examines the surface for visual damage such as marring.

Resistance of Organic Coatings to the Effects of Rapid Deformation (Impact)—ASTM Method D 2794

Drop a standard weight (four pounds (lbs) (8.8 kilograms (kg)) a distance onto an indenter that deforms both cured film and the substrate or panel underlying the cured film or coating. The indenter can be placed either against the cured film to impose an intrusion and evaluate resistance to direct impact or against the substrate or panel surface opposite that on which the cured coating is bonded to impose an extrusion force to evaluate resistance to a reverse impact. Gradually increase the distance the weight drops until reaching a distance at which coating failure occurs. Cured films or coatings generally fail by cracking, which becomes more visible evident when viewed through a magnifier, especially after one applies an acidic copper sulfate solution to the cured film or coating after deformation.

The following examples illustrate, but do not limit, the present invention. All parts and percentages are based upon weight, unless otherwise stated. All temperatures are in ° C. Examples (Ex) of the present invention are designated by Arabic numerals and Comparative Examples (Comp Ex) are designated by capital alphabetic letters. Unless otherwise stated herein, "room temperature" and "ambient temperature" are nominally 25° C.

EX 1

Preparation of an Amide Triol from Diethanolamine and Methyl 11-Hydroxyundecanoate Subject methyl 10-undecenoate (commercially available from Aldrich) to reductive hydroformylation to prepare methyl 11-hydroxyundecanoate using procedures previously incorporated herein by reference, especially U.S. Pat. No. 4,496,487 at column 4, lines 9-19.

Place 158.4 grams (g) (0.7322 mole) of methyl 11-hydroxyundecanoate, 154.8 g (1.472 mole) diethanolamine; 2.6 g (0.39 mole) of an 85 wt % solution of potassium hydroxide (in methanol) and 140 milliliters (ml) of toluene in a 500 ml round bottom flask equipped with a magnetic stirring bar and a water-cooled reflux condenser. Seat the flask in a sand bath in an electric heating mantle. Control sand bath temperature using a temperature controller connected to a thermocouple immersed in the sand bath. With the sand bath, heat contents of the flask to 60° C., with stirring, whereby solid components of the flask contents dissolve in the toluene to yield a clear, colorless solution.

Maintain the solution temperature at 60° C. with continued stirring for 24 hours before taking a sample of the solution and subjecting the sample to Fourier Transform Infrared (FTIR) analysis. The analysis shows a trace amount of ester absorbance as indicated by a small peak at 1729 cm$^{-1}$.

Add another 10.2 g (0.1 mole) of diethanolamine and maintain the temperature at 60° C. with continued stirring for 18 hours before allowing contents of the flask to cool to room temperature. Subject contents of the flask to rotary evaporation at a temperature of 35° C. and a vacuum of 4 inches of mercury (Hg) (15 kilopascals (kPa)) for two hours to remove methanol produced during reaction of the vessel contents, thereby leaving a solid reaction product.

Add 350 ml of an aqueous 2 wt % solution of sodium chloride (NaCl) to the flask and stir contents of the flask (solid reaction product and aqueous NaCl solution) for three hours. Vacuum filter contents of the flask through a coarse glass-fritted Buchner funnel. Rinse solid contents of the funnel with 100 ml of the 2% aqueous NaCl solution and then repeat stirring of the solid contents with 350 ml of fresh 2% aqueous NaCl solution for three hours. Repeat filtration through the Buchner funnel and then rinse solid contents of the funnel first with two 100 ml aliquots of fresh 2% aqueous NaCl solution and then with two 100 ml aliquots of deionized water.

Allow the solid contents to air dry in a fume hood for three days. The dried solid contents have a weight of 180.7 g. Place the dried solid contents and 500 ml toluene into a mixing vessel and mix them for two hours. Vacuum filter contents of the mixing vessel through a coarse glass-fritted Buchner funnel, then rinse solid contents of the funnel with two 200 ml aliquots of toluene before air drying the solid contents overnight. Subject the dried solid contents to rotary evaporation until the contents in the form of a white powder show a constant weight. The constant weight, 158.9 g, represents a yield of 75% of theoretical.

Analysis of the white powder by FTIR, hydrogen nuclear magnetic resonance ($^1$H NMR) spectroscopy and carbon-13 NMR ($^{13}$C NMR) spectroscopy supports an amide triol structure as shown in Formula VI below.

Formula VI. Experimental Amide Triol

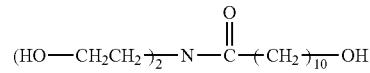

EX 2

Acrylation of the Amide Triol of Ex 1

Place 41.6 g (0.144 mole; 0.431 hydroxy (OH) equivalents) of the amide triol of Ex 1 and 200 ml of toluene in a 1-liter round bottom flask equipped with a mechanical stirring and a reflux condenser cooled to a temperature of −5° C. with a water-ethylene glycol mixture. Cool contents of the flask to a temperature of 7° C. using an ice bath before adding 46.82 g (0.517 mole) of acryloyl chloride and another 50 ml of toluene to the flask. Dropwise add 58.62 g (0.453 mole) of N,N-diisopropylethylamine to the flask over a 15 minute period while maintaining the ice bath at 7° C. Add a second 50 ml aliquot of toluene to the flask, then remove the ice bath and stir contents of the flask for 24 hours.

Using a separatory funnel, wash the toluene layer once with 200 ml of aqueous 2% NaCl solution and then twice with 200 ml aliquots of an aqueous 3% solution of sodium hydrogen carbonate (NaHCO$_3$). Dry the washed toluene layer with sodium sulfate (Na$_2$SO$_4$) and then vacuum filter the washed and dried toluene layer through a medium glass-fritted Buchner funnel. Add 0.1 g of 4-methoxyphenol in 5 ml of methanol (MeOH) to the filtrate, then subject the filtrate to rotary evaporation for 5.5 hours at 40° C. and 9 mm of Hg (1.2 kPa) to yield a toluene-free residue. Add 200 ml of anhydrous methanol to the residue with stirring and then separate solids from liquid filtrate using No. 1 filter paper. Subject the liquid filtrate to rotary evaporation at 40° C. and 9 mm of Hg to remove the methanol and yield a clear liquid final product. The final product weighs 66.07 g, which equates to a yield that is 74.0% of theoretical and has a viscosity at 25° C. of 110 cps (0.11 Pa·s) as measured by a I.C.I. cone and plate rheometer in accord with American Society for Testing and Materials (ASTM) procedure D4287. FTIR and $^1$H NMR analyses of the final product support an amide acylate structure as shown in Formula VII below.

Formula VII. Experimental Amide Triacrylate

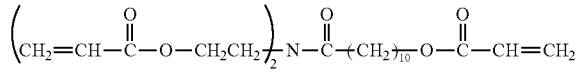

EX 3

Preparation of UV Cured Coatings Using the Amide Triacrylate of Ex 2

In a glass bottle, combine, with stirring, 8.727 g of the amide triacrylate of Ex 2, 0.24 g of a 50/50 blend of benzophenone and 1-hydroxycyclohexyl phenyl ketone (IRGACURE™ 500, commercially available from Aldrich), 0.2 g of methyldiethyl amine, two drops of polysiloxanes (BYK™ 307, commercially available from BYK Chemie, Japan Ltd.), and four drops of a nonsilicone defoaming agent (BYK™

A-555, commercially available from BYK Chemie, Japan Ltd.) to yield a formulated coating solution with a viscosity of 120 cps (0.12 Pa·s) at 25° C.

Using a number (No.) 32 BYK-Gardner draw down bar, draw or deposit coatings of the formulated coating solution on aluminum panels held in place by a clipboard. The coatings have a thickness of 2 to 3 mils (0.05 millimeter (mm) to 0.08 mm). Cure the coatings by passing the coated panels under a mercury lamp (H-bulb type lamp, UV Process Supply Inc., Part Number HS6808A4C-410) spaced 3.5 inches (in.) (7.6 centimeters (cm)) above the coated panels at a rate of 10 feet per minute (fpm) ($5.08 \times 10^{-2}$ meters per second (m/s)). The mercury lamp has an irradiation temperature of 101° Fahrenheit (° F.) (38.3° C.).

Determine cured coating glass transition temperature ($T_g$) via differential scanning calorimetry (DSC) using a programmed heating rate of 10° C. per minute. Skilled artisans recognize $T_g$ of a material as that point on a DSC plot where a sharp change in material heat flow occurs as the material transitions from a glassy state to a rubbery state. Evaluate pencil hardness in accord with ASTM D3363 as explained above. The coating $T_g$ and pencil hardness are, respectively, 29° C. and HB.

Ex 3 demonstrates that an amide acylate representative of the present invention yields a UV curable coating composition with a commercially acceptable working viscosity of less than or equal to 4,000 cps (4.0 Pa·s). Once deposited and cured, the coating has a commercially desirable $T_g$ of more than 25° C. The pencil hardness of HB amply meets requirements for many applications, especially for wood coatings where a hardness in excess of 6B is desired and a hardness of 2B or higher is preferred. Skilled artisans can readily determine if a hardness of HB is sufficient for their particular end use application.

EX 4

Preparation of UV Cured Coatings from a Blend of an Epoxy Acrylate and the Amide Triacrylate of Ex 2

Replicate Ex 3 with several changes. As a first change, decrease the amount of amide triacrylate to 5.168 g, add 7.517 g of an experimental bisphenol A epoxy acrylate (viscosity at 25° C. of 19,000 cps (19 Pa·s), density of 1.11 to 1.15 grams per cubic centimeter (g/cc) and an epoxy acrylate content of 3.6 millimoles per gram, formerly available from The Dow Chemical Company under the trade designation XZ 92554.00, and place the bottle containing the epoxy acrylate and amide triacrylate on a shaker manufacture by Eberbach Corporation under a heat lamp that is spaced 6 inches (in.) (15.2 cm) from the bottle and exposes the bottle to a temperature of approximately 50° C. for a period of 15 minutes to obtain a clear, homogeneous mixture. Then add, with stirring, 0.35 g of the same IRGACURE™ as in Ex 3, 0.30 g of methyldiethyl amine, two drops of BYK™ A-555 and one drop of BYK™ 307 to yield a formulated coating composition with a viscosity of 900 cps (0.9 Pa·s). Summarize $T_g$ and pencil hardness data in Table 1 below. A bisphenol A epoxy acrylate material believed to be comparable to the no longer available material noted above is SARTOMER™ CN104 (Sartomer Company, viscosity at 25° C. of 18,900 cps (18.9 Pa·s).

COMP EX A

Preparation of UV Cured Coatings Based on a Blend of an Epoxy Acrylate and Tri(Propylene Glycol)Diacrylate Replicate Ex 4 with several changes. First, increase the amount of bisphenol A epoxy acrylate to 22.6 g and substitute 15.067 g of tri(propylene glycol) diacrylate (Aldrich Chemical Company) for the amide triacrylate of Ex 2. Second, increase the time on the shaker to 20 minutes. Third, increase the amounts of IRGACURE™ 500 and methyldiethyl amine, respectively, to 1.02 g and 0.87 g and double the amounts of both BYK™ 307 and BYK™555. Summarize $T_g$ and pencil hardness data in Table 1 below.

TABLE 1

Properties of UV Cured Coatings

| Ex/ Comp Ex | Cure Rate (fpm) | Cure Rate m/s | Fingernail Scratch Test | Pencil Hardness | Methyl Ethyl Ketone Double Rubs |
|---|---|---|---|---|---|
| 4 | 5 | $25.4 \times 10^{-3}$ | Passed | 2H | >200 |
| A | 5 | $25.4 \times 10^{-3}$ | Passed | 2B | >200 |
| 4 | 25 | $127 \times 10^{-3}$ | Passed | 2B | >200 |
| A | 25 | $127 \times 10^{-3}$ | Failed | 2B | >200 |
| 4 | 30 | $152.4 \times 10^{-3}$ | Passed | 2B | >200 |
| A | 30 | $152.4 \times 10^{-3}$ | Failed | 2B | >200 |
| 4 | 35 | $177.8 \times 10^{-3}$ | Failed | 2B | >200 |
| A | 35 | $177.8 \times 10^{-3}$ | Failed | 2B | >200 |

The data presented in Table 1 show that amide acylates of the present invention, as illustrated by the amide acylate of Ex 2, function as satisfactory diluents for an epoxy acrylate in UV curable formulations. At low cure rates such as 5 feet per minute (fpm) ($25.4 \times 10^{-3}$ m/s), the amide acylates provide an increase in pencil hardness relative to a conventional acrylate diluent, in this case tri(propylene glycol)diacrylate. At faster cure rates of 25 fpm ($127 \times 10^{-3}$ m/s) or 30 fpm ($152.4 \times 10^{-3}$ m/s), amide acylates also provide improved scratch resistance relative to the same conventional acrylate diluent. If scratch resistance is of little or no importance, as in an ink application, one may use compositions of the present invention with even higher cure rates of 35 fpm ($177.8 \times 10^{-3}$ m/s) or more.

EX 5

Preparation of a UV Curable Ink Composition Based on the Amide Triacrylate of Ex 2

Prepare a pigment concentrate by passing a combination of four materials through a three roll mill five times. The materials and amounts, based upon concentrate weight, are: 37.15 wt % of blue pigment (Phthalo Blue 249-3054, Sun Chemical), 37.15 wt % of the amide triacrylate of Ex 2, 15.7 wt % of a modified polyester acrylate (FLEXCURE™ D30, Ashland), and 10.0 wt % trimethylolpropane triacrylate (SARTOMER SR™-351, Sartomer Company).

Prepare a coating ink by hand mixing the following components in a jar: 32.1 parts by weight (pbw) of the pigment concentrate; 45.5 pbw of a proprietary polyester acrylate (SARTOMER CN™ 2273, Sartomer Company); 10.3 pbw of the same trimethylolpropane triacrylate as in the pigment concentrate; 0.5 pbw of an acrylic polymer flow control additive (RESIFLOW™ LG-99, Estron Chemical Co.); and 9.2 pbw of a phosphine oxide, alphahydroxy ketone and a benzophenone derivative (SARCURE SR™ 1135, Sartomer Company).

Use a Pamarco hand proofer fitted with a 550 laser engraved ceramic anilox printing roller and having a screen with a volumetric capacity of 4.19 cubic centimeters per square meter ($cm^3/m^2$) to draw ink onto a variety of substrates and form proofs. The substrates are 80 pound (176 kg) Centura Gloss, foil, paper stock brushout charts (commercially available from Leneta under the trade designation 5DX), and polyester film.

The procedure for using the hand proofer is as follows: (a) place the stock to be printed on a smooth, clean and flat surface; (b) adjust position of the printing roller to a desired setting and lock it in this position with small thumb screws; (c) drop about ½ teaspoonful (2.5 ml) of the ink or coating to be proofed on top of a nip located between the printing roller and a second, stock-contact rubber roller; (d) spin the rolls by hand in order to fully "ink up" the anilox roll; and (e) hold the proofer so that the rubber roller rests on the stock and draw it toward the operator, using a smooth, even, moderately fast stroke with just enough pressure to turn the rollers without slippage.

Cure the inks by passing the proofs through a Hanovia UV-6 conveyer unit equipped with a 300 watt H bulb at a line speed of 200 fpm (1.01 m/s). An evaluation of the ink on the cured proofs shows that the ink is very glossy and has a strong blue color with no visually discernible haze.

COMP EX B

Preparation of a UV Curable Ink Composition Based on Commercially Available Polyester Acrylates Replicate Ex 6, but substitute a proprietary polyester acrylate (SARTOMER CN™ 2270, Sartomer Company) for the amide triacrylate of Ex 2 when preparing the pigment concentrate. An evaluation of the ink on the cured proofs shows that, relative to the cured proofs of Ex 5, the cured ink of Comp Ex B appears to be less dense and less transparent than the cured ink of Ex 5.

EX 6

Preparing a Ring-Opened Epoxidized Soybean Oil

Add 250 g of an epoxidized soybean oil (ESO) (FLEXOL™ Plasticizer, EPO, 7.0 wt % epoxide oxygen, approximately 1.09 mole epoxide, commercially available from The Dow Chemical Company) and 250 g (7.8 mole) of methanol (MeOH) to a 1-liter, three-necked round bottom flask equipped with a mechanical stirrer and a heating mantle. Fit one neck with a condenser topped with a nitrogen/vacuum inlet. Fit a second neck with a thermocouple probe connected to an electronic temperature controller. Plug the third neck. While stirring flask contents (ESO and MeOH) at a stir speed of 300 revolutions per minute (rpm), evacuate the flask and back fill it with nitrogen three times to remove air from the flask and replace it with a gaseous nitrogen atmosphere. Heat the flask contents, with continued stirring at the same speed, to a set point temperature of 65° C. During heating, the flask contents change into a clear, pale yellow, homogeneous solution at a temperature of about 50° C.

After the flask contents reach the set point temperature, add 38.1 g of ion exchange resin beads (DOWEX™ MSC-1, The Dow Chemical Company), previously washed with MeOH and air dried, to the flask. Increase the stir speed to 500 rpm while maintaining reactor contents at the set point temperature and continue stirring at that speed for 18 hours. Stop stirring and allow flask contents, a clear, homogeneous, pale yellow solution and ion exchange resin beads, to cool to room temperature (nominally 25° C.). Vacuum filter the flask contents to separate the solution (filtrate) from the ion exchange resin beads. Vacuum distill the filtrate with a nitrogen sweep using a rotary evaporator with a bath operating at a set point temperature of 60° C. while gradually (over a time span of approximately one hour) decreasing pressure to a pressure within a range of from 10 to 15 millimeters of mercury (mm Hg) (1.3 to 2 kPa). After one hour at the set point temperature and decreased pressure, increase the set point temperature to 70° C. and maintain that temperature for two hours with a slight vacuum sweep before turning off the vacuum and heating and allowing the vacuum-distilled filtrate to cool to room temperature and pressure.

Analyze the vacuum-distilled filtrate, a clear, light golden yellow oil, for hydroxy group via titration using ASTM Test Method D4274. This method is based on back titrating with 1.0 normal (N) sodium hydroxide (NaOH) after reacting an aliquot of the filtrate with a known excess of phthalic anhydride.) The oil has a hydroxy group content of 5.16 wt %.

EX 7

Acrylation of the Ring-Opened ESO of Ex 6

With several changes, replicate Ex 2 to acylate the ring-opened ESO of Ex 6. First, use 60 g (0.1819 hydroxy (OH) equivalents) of the ring-opened ESO of Ex 6 rather than the amide triol of Ex 1 and 200 ml of toluene and reduce the amount of acryloyl chloride to 24.7 g (0.2183 mole). Also, reduce the amount of N,N-diisopropylethylamine to 24.7 g (0.191 mole), but increase the time of addition to 50 minutes while maintaining the ice bath at a temperature within a range of from 6° C. to 9° C. In addition, remove the ice bath after adding the second 50 ml aliquot of toluene and reduce the stirring time from 24 hours to 22 hours.

Recover the final product, a clear liquid, as in Ex 2. The liquid has a viscosity of 1550 cps (1.55 Pa·s); and FTIR analysis indicates that an acylate structure is present in the liquid. This Ex 7 yields an acylate-containing, ring-opened ESO with a suitably low working viscosity of less than 4,000 cps (4.0 Pa·s). Skilled artisans desire to minimize working viscosity whenever possible, especially for ink applications.)

EX 8

Preparation of UV Cured Coatings Using the Product of Ex 7

With a number of changes, replicate Ex 3. First, use 18.38 g of the Ex 7 product rather than Ex 2 product and increase the amount of IRGACURE™ 500 to 0.50 g. In addition, decrease the amount of BYK™ to three drops. The formulated coating solution has a viscosity of 1525 cps (1.52 Pa·s).

Apply the formulated coating solution as in Ex 2, but use phosphated steel panels rather than aluminum panels, increase the irradiation temperature to 110° F. (43° C.) and decrease the cure rate to 5 fpm (2.54 m/s). Summarize cured coating properties in Table 2 below.

EX 9

Preparation of UV Cured Coatings from a Blend of an Epoxy Acrylate and the Product of Ex 7

Replicate Ex 4 with several changes. First, use 27.63 g of the product of Ex 7 rather than the amide triacrylate of Ex 3 and increase the amount of epoxy acrylate to 18.42 g. Also, increase the amount of IRGACURE™ 500 to 1.24 g, the amount of methyldiethyl amine to 1.06 g, the amount of BYK™ 307 to four drops and the amount of BYK™ A-555 to six drops. In addition, apply the formulated coating solution as in Ex 8 rather than according to the substrate and conditions of Ex 4. Summarize cured coating properties in Table 2 below.

COMP EX C

Replicate Comp Ex A, but change the amounts of epoxy acrylate and diacrylate to 15.92 g each, decrease the amounts of IRGACURE™ 500 to 0.86 g and methyldiethyl amine to 0.73 g. In addition, change the amounts of BYK™ 307 and BYK™ A-555 respectively to three drops and six drops. One must add the diacrylate in order to attain a desirable working viscosity of less than or equal to 4,000 cps (4.0 Pa·s) as the epoxy acrylate has an undiluted viscosity (at 25° C.) of 19,000 cps (19 Pa·s). In addition, apply and cure coatings as in Ex 8 rather than as in Comp Ex A. Summarize cured coating properties in Table 2 below. Report impact resistance values determined in accord with ASTM Method D2794 as explained above, in inch-pounds (in-lbs)/kilogram-meter (kg-m).

TABLE 2

| Ex/Comp Ex | Viscosity at 25° C. (cps/Pa·s) | Coating thickness (mils/mm) | Impact Resistance - Direct (in-lbs/kg-m) | Impact Resistance - Reverse (in-lbs./kg-m) | Pencil Hardness | Methyl Ethyl Ketone Double Rubs |
|---|---|---|---|---|---|---|
| 8 | 1525/1.52 | 2.44/0.062 | 48/2.7 | 2/0.11 | <4B | 175 |
| 9 | 4000/4.0 | 2.60/0.066 | 72/4.0 | 10/0.56 | HB | >200 |
| C | 700/0.7 | 2.20/0.56 | 40/2.2 | <2/<0.11 | 2H | >200 |

The data in Table 2 show that the acylate-containing, ring-opened ESO of Ex 7 provides improved impact resistance when used as a reactive diluent as in Ex 9 relative to a conventional acrylate diluent (tri(propylene glycol)diacrylate or TPGDA) as in Comp Ex C, even at a higher viscosity. While the ratio of reactive diluent to bisphenol A epoxy acrylate is nearly the same for both Ex 9 and Comp Ex C, the amount of reactive diluent (Ex 7) in Ex 9 is slightly greater relative to the bisphenol A epoxy acrylate than in Comp Ex C in order to drop composition viscosity to 4,000 cps (4.0 Pa·s). A further increase in amount of the reactive diluent of Ex 7 relative to bisphenol A epoxy acrylate should lead to a further decrease in composition viscosity. The data in Table 2 relative to Ex 8 also show that, even without bisphenol A epoxy acrylate, a cured coating based upon the acylate-containing, ring-opened ESO of Ex 7 provides impact resistance at least equal to that of a fully formulated conventional coating that contains bisphenol A epoxy acrylate as in Comp Ex C. The composition of Ex 8 can also be used as formulated in the absence of TPGDA or some other reactive diluent because of its desirably low viscosity relative to that of the bisphenol A epoxy acrylate.

EX 10

Preparation of an Amide Triol Based on 12-Hydroxymethyl Stearate

Weigh 200 g of 12-hydroxymethyl stearate (PARACIN™ 1, CasChem of Rutherford Chemicals) and 276.0 g of diethanolamine into a 2000 ml, 3-necked flask equipped with a heating mantle, thermocouple, mechanical stirrer and a sparger. Heat the flask and its contents to a set point temperature of 120° C. Maintain the contents of the flask at that temperature while mixing the contents and subjecting them to a subsurface nitrogen purge for 30 minutes. Continue mixing, but change the subsurface purge to a headspace purge and maintain these conditions overnight.

Allow flask contents to cool to room temperature (nominally 25° C.) and then add 1000 ml of chloroform to the flask to convert the contents to a chloroform solution. Wash the solution four times with 700 g of deionized water, then dry the solution with 75 g of magnesium sulfate ($MgSO_4$). Isolate product from the solution via rotary evaporation as in Ex 1. The product, a solid at room temperature weighs 216.7 g, equating to a yield of 88.6% of theoretical. Analysis of the product as in Ex 1 is consistent with an amide triol structure.

EX 11

Acrylation of the Amide Triol of Ex 10

Weigh 400 g of diethyl ether, 95.0 g of the amide triol of Ex 10 and 72.0 g of acryloyl chloride into a 2000 ml, 3-necked flask that is immersed in an ice bath and equipped with a addition funnel, thermocouple, mechanical stirrer and a nitrogen head space purge tube. Activate the mechanical stirrer to stir contents of the flask. Weigh 96.9 g of N,N-diisopropylethylamine into the addition funnel and feed it dropwise to the stirred contents over a 100 minute interval.

Remove the ice bath, add 250 g of diethyl ether to the flask to form a mixture and stir the mixture at ambient temperature overnight. Then add 150 g of diethyl ether and 1000 ml of deionized water to the flask and continue stirring for 60 minutes.

Transfer contents of the flask to a separatory funnel to effect phase separation into an aqueous layer and a liquid organic layer, then discard the aqueous layer. Wash the liquid organic layer twice with 170 g of a 5 wt % aqueous NaCl solution, twice with 170 g of a 5 wt % aqueous $H_2SO_4$ solution and finally twice with 170 g of a 5 wt % aqueous $NaHCO_3$ solution, before drying it with 25 g of $MgSO_4$. Add 0.12 g of 4-methoxyphenol to the washed and dried organic liquid, then isolate a liquid product via rotary evaporation as in Ex 10. The liquid product weighs 97.8 g, representing a yield of 73.3% of theoretical, and has a viscosity of 250 cps (0.25 Pa·s). $^1$H NMR and FTIR analyses of the product confirm the presence of an amide triacrylate structure.

EX 12

Preparation of Ricinolamide Triol

Replicate Ex 10 with several changes to prepare a ricinolamide triol. First, substitute 200.1 g of castor oil for 12-hydroxymethyl stearate. Second, use 400 g of 5 wt % aqueous NaCl solution for each wash and decrease the amount of MgSO4 to 20 g. The recovered product weighs 195.5 g, representing a yield of 78.0% of theoretical. $^1$H NMR and FTIR analyses of the product are consistent with a ricinolamide triol structure.

EX 13

Acrylation of the Ricinolamide Triol of Ex 12

Replicate Ex 11 with changes. Begin by weighing 200 g of diethyl ether, 47.5 g of the product from Ex 12 and 36.9 g of acryloyl chloride into a 1000 ml, 3-necked flask that is sited and equipped in the same manner as the 2000 ml flask of Ex 11. Reduce the amount of N,N-diisopropylethylamine to 50.5 g and the amount of diethyl ether to 139 g.

Rather than the amounts of diethyl ether and deionized water and the mixing time specified in Ex 11, add 96 g of diethyl ether and 500 g of a 3 wt % aqueous NaHCO$_3$ solution and reduce the mixing time to 30 minutes.

After discarding the aqueous layer, change the product recovery procedure. Begin by adding 210 g of diethyl ether to the organic layer to form a dilute organic layer, then wash the dilute organic layer three times with 150 g of a 5 wt % aqueous NaHCO$_3$ solution before drying it with 10 g of MgSO$_4$. Halve the amount of 4-methoxyphenol added before product isolation by rotary evaporation. The product weighs 51.1 g, representing a yield of 75.8% of theoretical, and has a viscosity of 193 cps (0.19 Pa·s). $^1$H NMR and FTIR analyses of the product are consistent with a ricinolamide acylate structure.

EX 14

Preparation of an Amide Triol from Diethanolamine and 12-Hydroxymethyl Methyl Stearate Prepare a product that contains 12-hydroxymethyl methyl stearate by reductive hydroformylation of methyl oleate using procedures outlined in U.S. Pat. No. 4,496,487, the teachings of which are incorporated herein to the maximum extent permitted by law. Subject that product to distillation to remove volatile components and yield a reactant with a 12-hydroxymethyl methyl stearate content of 94 wt %, based upon reactant weight.

Prepare an amide triol based on 12-hydroxymethyl methyl stearate by replicating Ex 10 with changes. Change the apparatus by substituting a Dean-Stark trap with condenser and nitrogen head space purge tube for the sparger of Ex 10. Weigh 400.0 g of the 94 wt % 12-hydroxymethyl methyl stearate-containing reactant prepared above and 511.7 g of diethanolamine into the flask. Add a solution of 0.93 g of potassium hydroxide (KOH) in 10 ml of methanol (MeOH) before heating the contents of the flask to a set point temperature of 110° C. and maintaining that temperature with stirring overnight.

Use a modified product recovery process, relative to that of Ex 10. Begin by substituting toluene for the chloroform. Change the wash procedure to washing three times with 1600 g of a 2 wt % aqueous NaHCO$_3$ solution and dry with 80, rather than 75, g of MgSO$_4$.

Product recovery via rotary evaporation under reduced pressure at a set point temperature of 60° C. yields a liquid that weighs 450 g, representing a yield of 92.0% of theoretical. $^1$H NMR and FTIR analyses of the product were consistent with a amide triol structure.

EX 15

Acrylation of the Amide Triol of Ex 14

Replicate Ex 11 with changes. Begin by weighing 704 g of diethyl ether, 180.1 g of the amide triol from Ex 14 and 139.2 g of acryloyl chloride were weighed into the 2000 ml, 3-necked flask of the apparatus of Ex 11. Increase the amount of N,N-diisopropylethylamine to 174.1 g and add it as in Ex 11, but over a 220 minute period of time.

Remove the ice bath and stir the mixture at ambient temperature (nominally 25° C.) overnight, but do not add any diethyl ether before stirring overnight. After stirring overnight, add 260 g diethyl ether and 400 g of a 2 wt % aqueous NaCl solution to contents of the flask.

Modify the recovery procedure of Ex 11 by saving both the aqueous layer and the organic layer after phase separation. Wash the organic layer four times with 400 g of a 5 wt % aqueous NaHCO$_3$ solution and set the washed organic layer aside. With stirring, add 400 g of deionized water and 116 g of diethyl ether to the saved aqueous layer, then stop stirring and allow phase separation into an aqueous layer and an ether layer to occur in a separatory funnel.

Wash the ether layer with 400 g of a 5 wt % aqueous NaHCO$_3$ solution, allow the washed ether layer to rest overnight, then wash it three more times with 400 g of the NaHCO$_3$ solution. Combine the washed ether layer with the previously set aside washed organic layer and dry the combined layers with 30 g MgSO$_4$. Add 0.32 g of 4-methoxyphenol to the dried organic/ether layer combination and recover a liquid product via rotary evaporation as in Ex 11. The product has a viscosity of 250 cps (0.25 Pa·s) and, per $^1$H NMR and FTIR analyses, is consistent with an amide triacrylate structure.

EX 16

Preparation of an Amide Polyol from a Ring-Opened ESO

Replicate the process of Ex 10 with changes to prepare an amide polyol based upon a ring-opened ESO. Begin by weighing 232.6 g of a ring opened epoxidized soybean oil prepared as in Example 6 and 200.3 g of diethanolamine into the apparatus of Ex 10. Reduce the set point temperature to which the flask and its contents are heated to 110° C.

After allowing flask contents to cool to room temperature, add 600 ml of toluene, rather than 1000 ml of chloroform, to convert the contents to a toluene solution. Change the wash and dry procedure by starting with two washes with 1000 g of deionized water, continue with two washes with 1000 g of a 3 wt % aqueous NaCl solution, before drying with 160 g of MgSO$_4$. Isolate product from solvent (toluene) by rotary evaporation under reduced pressure at 60° C. as in Ex 1. The isolated product weighs 209.7 g and, by $^1$H NMR and FTIR analyses, has a structure consistent with that of an amide polyol.

EX 17

Acrylation of the Amide Polyol of Ex 16

Use the apparatus of Ex 13 and a modification of the process described therein to acylate the amide polyol of Ex 16. Substitute the amide polyol of Ex 16 for the product of Ex 12 and reduce the amount of acryloyl chloride to 36.1 g. Reduce the amount of N,N-diisopropylethylamine to 47.9 g and feed it dropwise over a time interval of 110 minutes.

After removing the ice bath, add 150 g of diethyl ether with stirring and allow stirring to continue overnight at ambient temperature before adding another 150 g of diethyl ether together with 500 ml of deionized water while continuing stirring for 45 minutes.

After discarding the aqueous layer, use a modified procedure to recover the acylated amide polyol. First, wash the organic layer twice with 110 g of a 5 wt % aqueous NaCl solution, then twice with 110 g of a 5 wt % aqueous solution of sulfuric acid ($H_2SO_4$) and twice with 110 g of a 5 wt % aqueous $NaHCO_3$ solution before drying the organic layer with 15 g of MgSO4. Add 0.07 g of 4-methoxyphenol and isolate the product via rotary evaporation under reduced pressure and at ambient temperature to yield 46 g of product (69.8% of theoretical yield). The product has a viscosity of 650 cps (0.65 Pa·s) and, per $^1$H NMR and FTIR analyses, is consistent with an acylated amide polyol structure.

EX 18

Preparation of an Acylate from a Polyester Derived from 12-Hydroxymethyl Methyl Stearate Into a 2-liter glass reactor flask, charge 1050.3 grams (3.15 moles) of soy monomer and 328.9 grams (0.53 moles) of ethoxylated glycerin as initiator. Seal the flask and degas it with a gaseous nitrogen sparge under a vacuum of 20 torr (2.67 kPa) while heating contents of the flask to a set point temperature of 50° C. Briefly break the vacuum and add 0.78 grams (565 ppm) of stannous octanoate to the flask. Reinitiate the vacuum of 20 torr (2.67 kPa), remove or disconnect nitrogen sparging and heat the flask and its contents to a set point temperature of 195° C. and maintain the flask and its contents under such conditions for a period of 4 hours, collecting methanol (MeOH) byproduct in a dry ice trap. As an alternative, one may also use a vacuum, a nitrogen sparge or any combination of the two to effect MeOH removal. After the four hour period, release the vacuum and allow the reactor flask and its contents to cool to room temperature overnight under nitrogen. Add 0.77 g (558 parts by weight per million parts by weight of flask contents (ppm)) of stannous octanoate and connect a nitrogen sparge tube to the reactor flask. Heat the flask and its contents to a set point temperature of 195° C. with a slow nitrogen sparge for 4 hours to complete the reaction.

Using the same apparatus as in Ex 17 and a modification of the process of Ex 17, synthesize a polyester acylate using the polyester prepared in the immediately preceding paragraph. Begin the modified process by weighing 700 ml of toluene, 200 g of the polyester (OH equivalent weight of 398.6 (OH equivalent weight.=1701 divided by % hydroxy, with % hydroxy being determined via titration in accord with ASTM Test Method D4274) and 54.5 g of acryloyl chloride into the flask. Increase the amount of N,N-diisopropylethylamine to 68.1 g, but decrease the time of addition to 100 minutes.

Remove the ice bath as in Ex 17, but add no further ingredients before stirring the mixture at ambient temperature overnight. Before effecting separation, add 400 g of a 3 wt % aqueous NaCl solution to the flask. After separation using the separatory funnel, discard the aqueous layer as in Ex 17 and wash the organic (toluene) layer three times with 400 g of a 3 wt % aqueous $NaHCO_3$ solution and once with 400 g of deionized water before drying the organic layer with 119.4 grams of $Na_2SO_4$. Add 0.29 g of 4-methoxyphenol to the washed and dried organic layer then isolate product from toluene by rotary evaporation as in Ex 17, but at a temperature of 40° C. The isolated product is a liquid, weighing 188.8 g, representing a product yield of 83.1% of theoretical. The product has a viscosity of 550 cps (0.55 Pa·s) and, has, a structure consistent with a polyester acylate in accord with $^1$H NMR and FTIR analyses.

EXAMPLE 19

Preparation of a Mono-Acylate from 12-Hydroxymethyl Methyl Stearate

Using the same apparatus as in Ex 18 and a modification of the process of Ex 18, prepare a mono-acylate from 12-hydroxymethyl methyl stearate. Begin by weighing 700 ml of toluene, 200 g of 12-hydroxymethyl methyl stearate (prepared by reductive hydroformylation of methyl oleate as described above) and 66.1 g of acryloyl chloride into the flask. Increase the amount of N,N-diisopropylethylamine to 82.8 g, but reduce the time over which it is added dropwise via the addition funnel to 85 minutes.

Recover product as in Ex 18, but increase the amount of Na2SO4 to 127.6 g and decrease the amount of 4-methoxyphenol to 0.11 g. The recovered product weighs 231.5 g, representing a yield of 99.3% of theoretical, and has a viscosity of 12.5 cps (0.012 Pa·s). FTIR analysis of the product suggests a structure consistent with a mono-acylate.

EXAMPLE 20

Preparation of a Mono-Acylate from Methyl 11-Hydroxyundecanoate

Prepare a mono-acylate from methyl 11-hydroxyundecanoate using a same apparatus as in Ex 19, but with several modifications of the procedure of Ex 19. Begin the modified process by weighing 600 ml of toluene, 200 g of methyl 11-hydroxyundecanoate and 100.4 g of acryloyl chloride into the flask. Increase the amount of N,N-diisopropylethylamine to 125.5 g and the amount of time over which it is added dropwise via the addition funnel to 140 minutes.

Recover product as in Ex 19, but reduce the amount of $Na_2SO_4$ to 103.3 g and increase the amount of 4-methoxyphenol to 0.12 g. Recover the product, as in Ex 19. The resulting product weighs 244.5 g, representing a yield of 99.0 percent of theoretical and has a viscosity of 10 cps (0.02 Pa·s). 0.12 grams of 4-methoxyphenol was added to the toluene solution and the product was isolated by rotary evaporation of the solvent under reduced pressure at 40° C. 244.5 grams of product with a viscosity of 10 cps (0.01 Pa·s) was recovered. FTIR analysis of the product suggests a structure consistent with a mono-acylate structure.

The novel acylate materials of the present invention, especially those of Ex 11, 13, 15 and 17-20, have very low viscosities that range from 10 cps (0.01 Pa·s) to 650 cps (0.65 Pa·s). Such low viscosities lead to improved processing in any of a variety of UV-curable applications such as inks and coatings. These materials are believed to be hydrophobic, thereby rendering them water-resistant, and, relative to currently available commercial materials, flexible. As such, these novel acylate materials are also believed to be suitable for use in improving both processability and performance of existing oligomers such as bisphenol A epoxy acrylate. In addition, certain of the novel acylate materials may effectively serve as a substitute for one or more oligomers.

Similar results are expected with other acylate materials, particularly amide acylate materials, prepared in accord with the teachings presented herein.

What is claimed is:

1. A process for preparing a reactive monomer composition comprising:
    a. reacting an alkanolamine with a compound having at least one reactive hydroxy group or moiety, the compound being selected from the group consisting of hydroxy-functionalized triglycerides, hydroxy-functionalized fatty acids and hydroxy-functionalized fatty acid esters, to convert the compound to an amide polyol; and
    b. reacting the amide polyol with an α, β-unsaturated acylating agent to convert the amide polyol to an amide poly-α, β-unsaturated acylate; and
    wherein the reactive monomer composition comprising an amide poly-α, β-unsaturated acylate represented by formula I:

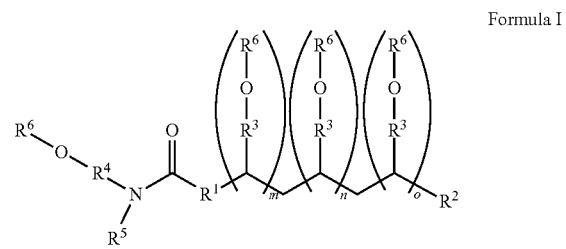

Formula I wherein $R^1$ is a hydrocarbylene moiety; $R^2$ is hydrogen or a hydrocarbyl moiety; $R^3$ is nil or a hydrocarbylene moiety; $R^4$ is a hydrocarbylene moiety; $R^5$ is H, a hydrocarbyl moiety or a moiety represented by Formula II:

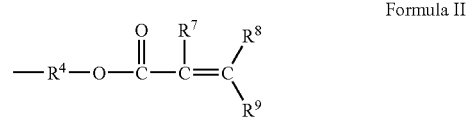

Formula II wherein $R^4$ is as defined above and $R^7$, $R^8$ and $R^9$ are independently hydrogen or a hydrocarbyl moiety; $R^6$ is a moiety having Formula III:

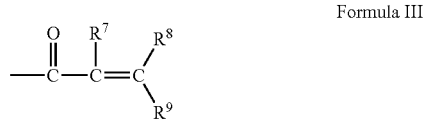

Formula III wherein $R^7$, $R^8$ and $R^9$ are independently defined as above; and m, n, and o are independently 0 or 1 provided, however that a sum of m, n and o is a positive integer greater than zero.

2. The process of claim 1, further comprising a precursor step of preparing the compound by at least partial reductive hydroformylation of a starting material selected from the group consisting of unsaturated vegetable oils, fatty acids and fatty acid esters.

3. The process of claim 2, wherein the starting material is at least one vegetable oil and the vegetable oil is an unsaturated oil selected from the group consisting of safflower oil, sunflower oil, soybean oil, linseed oil, peanut oil, olive oil, tobacoseed oil, cottonseed oil, coconut oil, rapeseed oil, canola oil, corn oil, and lesquerella oil and modified versions of such oils.

4. The process of claim 2, wherein the starting material is at least one unsaturated methyl ester selected from the group consisting of methyl oleate, methyl 10-undecenoate, methyl 9-decenoate, methyl linolenate, and methyl linoleate.

5. The process of claim 1, wherein the compound is at least one member selected from the group consisting of castor oil, ricinoleic acid or a ricinoleic acid ester.

6. The process of claim 1, wherein the compound is hydroxymethyl stearate or hydroxymethyl methyl stearate.

7. The process of claim 1, wherein the α, β-unsaturated acylating agent is at least one of ethyl acrylate, methyl methacrylate, or an acid halide selected from the group consisting of acryloyl chloride or methacryloyl chloride.

8. The process of claim 1, wherein the alkanolamine is at least one of ethanolamine, 1,2-propanolamine or diethanolamine.

9. The process of claim 1, wherein the reactive monomer composition comprises an amide poly-a,b-unsaturated acylate represented by formula I, wherein $R^1$ is a hydrocarbylene moiety; $R^2$ is a hydrogen or hydrocarbyl moiety; $R^3$ is nil or methylene; $R^4$ is ethylene or propylene, $R^5$ is hydrogen, methyl or a moiety represented by Formula II wherein $R^4$ is ethylene, $R^7$ is hydrogen or methyl and $R^8$ and $R^9$ are hydrogen; and $R^6$ is a moiety represented by Formula III wherein $R^7$ is hydrogen or methyl and $R^8$ and $R^9$ are hydrogen.

\* \* \* \* \*